United States Patent
Kiyomori et al.

(10) Patent No.: US 7,834,120 B2
(45) Date of Patent: Nov. 16, 2010

(54) MONOFUNCTIONAL MONOMER HAVING CAGE OLIGOSILOXANE STRUCTURE AND METHOD OF MAKING

(75) Inventors: Ayumu Kiyomori, Joetsu (JP); Tohru Kubota, Joetsu (JP); Yasufumi Kubota, Joetsu (JP); Takayuki Honma, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 678 days.

(21) Appl. No.: 11/242,078

(22) Filed: Oct. 4, 2005

(65) Prior Publication Data

US 2006/0074213 A1 Apr. 6, 2006

(30) Foreign Application Priority Data

Oct. 5, 2004 (JP) .............................. 2004-292386

(51) Int. Cl.
*C08G 77/20* (2006.01)
(52) U.S. Cl. .............................. 528/37; 528/32; 528/39; 556/453; 556/456; 556/440
(58) Field of Classification Search .................. 528/37, 528/10, 33–34, 39; 556/400, 436, 450
See application file for complete search history.

(56) References Cited

U.S. PATENT DOCUMENTS

| | | | |
|---|---|---|---|
| 5,047,492 A | | 9/1991 | Weidner et al. |
| 5,128,431 A | * | 7/1992 | Riding et al. .................. 528/15 |
| 5,484,867 A | | 1/1996 | Lichtenhan et al. |
| 5,942,638 A | * | 8/1999 | Lichtenhan et al. ......... 556/460 |
| 6,100,417 A | * | 8/2000 | Lichtenhan et al. ......... 556/460 |
| 6,362,279 B2 | | 3/2002 | Lichtenhan et al. |
| 6,569,932 B2 | * | 5/2003 | Hsiao et al. .................. 524/269 |
| 6,653,365 B2 | | 11/2003 | Jia |
| 6,716,919 B2 | | 4/2004 | Lichtenhan et al. |
| 6,933,345 B1 | * | 8/2005 | Lichtenhan et al. ......... 525/101 |
| 2003/0055193 A1 | * | 3/2003 | Lichtenhan et al. ........... 528/10 |
| 2004/0068075 A1 | * | 4/2004 | Lichtenhan et al. ........... 528/15 |

FOREIGN PATENT DOCUMENTS

| | | |
|---|---|---|
| JP | 2-178291 | 7/1990 |
| JP | 6-329687 | 11/1994 |
| JP | 2000-298286 | 10/2000 |
| JP | 2004-83626 | 3/2004 |
| JP | 2004-189840 | 7/2004 |
| WO | WO 01/72885 A1 | 10/2001 |

OTHER PUBLICATIONS

Gomez-Romero, Pedro and Sanchez, Clement. Functional Hybrid Material; Wiley-VCH; Apr. 2004, 6th Revised , pp. 27-28.*
European Search Report dated Dec. 23, 2005.
Isao Hasegawa et al.; Synthesis of Silylated Derivatives of the Cubic Octameric Silicate Species Si8O20^8−; Faculty of Engineering, Gifu University, Gifu, 501-11, Japan; Synthesis and Reactivity in Inorganic and Metal-Organic Chemistry (1994), 24(7), 1099-110.
Fayna Mammeri, et al.; Modification and characterization of Si-based Nanobuilding Blocks Precursors for Hybrid Materials; Dipartimento di Ingegneria dei Materiali e Tecnologie Industriali, Universita di Trento, Trento, 38050, Italy; Materials Research Society Symposium Proceedings (2005), Volume Date 2004, 847 (Organic/Inorganic hybrid Materials-2004), 363-368.

* cited by examiner

*Primary Examiner*—Margaret G Moore
(74) *Attorney, Agent, or Firm*—Westerman, Hattori, Daniels & Adrian, LLP

(57) ABSTRACT

A novel monofunctional monomer having a cage oligosiloxane structure is represented by formula (1) wherein X is a polymerizable oxygen-containing $C_1$-$C_{40}$ group, $R^1$ is a $C_1$-$C_{20}$ saturated hydrocarbon group, $C_6$-$C_{20}$ aromatic hydrocarbon group, $C_1$-$C_{20}$ organoxy group or halogen atom, and R is a non-polymerizable monovalent $C_1$-$C_{40}$ hydrocarbon group which is optionally halogenated. The monomer has improved compatibility with various solvents and polymerizable monomers. A method for preparing the same is also provided.

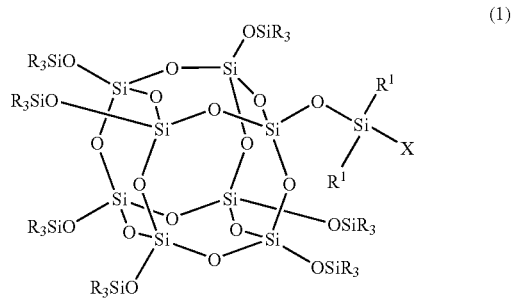

(1)

7 Claims, No Drawings

MONOFUNCTIONAL MONOMER HAVING CAGE OLIGOSILOXANE STRUCTURE AND METHOD OF MAKING

CROSS-REFERENCE TO RELATED APPLICATION

This non-provisional application claims priority under 35 U.S.C. §119(a) on Patent Application No. 2004-292386 filed in Japan on Oct. 5, 2004, the entire contents of which are hereby incorporated by reference.

TECHNICAL FIELD

This invention relates to novel monofunctional monomers having a cage oligosiloxane structure and methods for preparing the same.

BACKGROUND ART

Cage or polyhedral oligomeric siloxanes (oligosiloxanes) are structured such that various organic groups are positioned in the periphery of an inorganic core having a size of nanometer order. Efforts have been made to develop such cage oligosiloxanes which are useful as reinforcements, fire retardants or the like when added to organic polymers. For example, U.S. Pat. No. 6,362,279 describes a method for enhancing the fire retardancy of plastics by adding cage oligosiloxanes thereto. International Publication No. 01/72885 discloses to blend a cage oligosiloxane in a polymer by melt kneading for improving mechanical properties.

Aside from simple blending of a cage oligosiloxane with a polymer, there have been reported a number of attempts to combine a polymer with a cage oligosiloxane through covalent bonds for improving mechanical, thermal and other physical properties. For example, U.S. Pat. No. 5,484,867 describes the synthesis of polymers using cage oligosiloxanes having various polymerizable groups. Also U.S. Pat. No. 6,653,365 discloses as a dental material a composition comprising a cage oligosiloxane having a reactive group and a polymerizable resin.

In these patents, monofunctional polymerizable cage oligosiloxanes are used. If a difunctional or polyfunctional monomer or monomers are present in admixture, they become an unexpected cause of crosslinking, making it difficult to control the molecular weight and physical properties of the resulting polymers. The above-referred U.S. Pat. No. 5,484,867 describes that a high purity monofunctional cage oligosiloxane is prepared by reacting a cage heptasiloxane triol (referred to as T7-trisilanol, hereinafter) with a polymerizable organotrichlorosilane ($R^x$ is a polymerizable functional group) according to the following scheme A.

Scheme A:

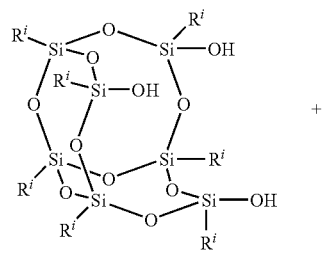

+

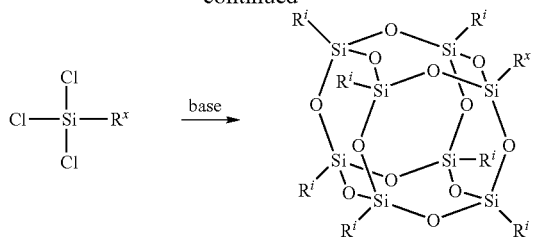

While it is inevitable to first prepare the precursor, T7-trisilanol, the type of substituent group ($R^1$ in scheme A) on silicon with which this compound can be isolated in high yields and in high purity is limited. Typical examples are isobutyl, cyclopentyl and cyclohexyl.

However, cage oligosiloxanes having alkyl or cycloalkyl groups substituted thereon are generally low soluble. Therefore, a large volume of solvent is necessary for the polymerization reaction of polymerizable cage oligosiloxanes having such substituent groups. In the case of copolymerization with another monomer, it is difficult to increase the ratio of a cage siloxane-containing monomer.

To the solubility of cage oligosiloxane, substituent groups on the silicon atoms forming a polyhedral skeleton have a substantial contribution. For example, JP-A 6-329687 is successful in improving the compatibility of a cage oligosiloxane with organopolysiloxane by introducing linear organooligosiloxy groups on silicon atoms.

It is, however, difficult to synthesize T7-trisilanol having such solubility-enhancing substituent groups. It is thus impossible to prepare a cage oligosiloxane having polymerizable functional groups $R^x$ by the method of scheme A.

As an alternative method, JP-A 2000-298286 describes that a polymerizable cage oligosiloxane is prepared by mixing two different organotrialkoxysilanes and subjecting them to hydrolysis and condensation, as shown by the following scheme B.

Scheme B:

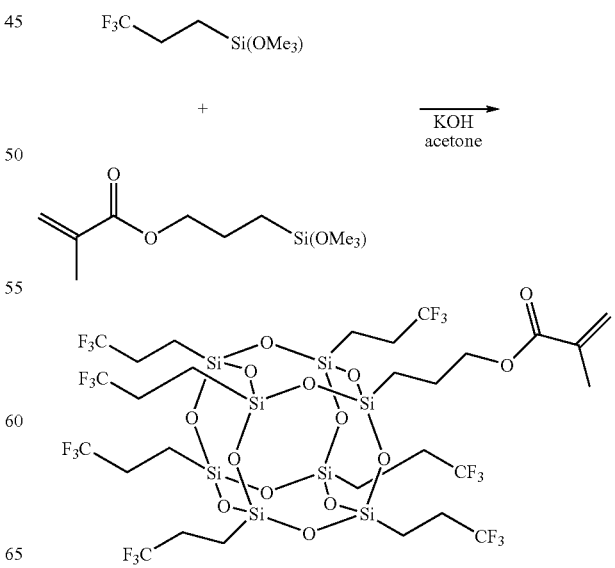

JP-A 2-178291 describes that a cage oligosiloxane having two types of organosiloxy group is obtained, through silylation of a cage ammonium silicate, by using two different silylating agents together or by effecting exchange reaction of organosiloxy groups bonded to silicon atoms forming a polyhedral skeleton. JP-A 2004-83626 and JP-A 2004-189840 disclose resin compositions comprising cage oligosiloxanes. Some cage oligosiloxanes are exemplified although the number of polymerizable groups is not specified. It is described that cage oligosiloxanes can be prepared through hydrolysis of trifunctional organosilicon monomers.

With these methods, however, the product is naturally a mixture of various siloxanes as demonstrated in Examples of JP-A 2-178291. Even if the desired monofunctional monomer is produced, its purification is difficult. It is thus difficult to obtain a monofunctional cage oligosiloxane of high purity.

There is a need for a method for preparing a polymerizable cage oligosiloxane having an increased solubility in high yields and high purity.

DISCLOSURE OF THE INVENTION

Therefore, an object of the invention is to provide a novel monofunctional monomer with a cage oligosiloxane structure having improved solubility in and compatibility with various solvents and compounds; and a method for preparing the same.

The inventors have discovered a novel monofunctional monomer having a cage oligosiloxane structure and a method for preparing the same.

In a first aspect, the invention provides a monofunctional monomer having a cage oligosiloxane structure, represented by the following general formula (1).

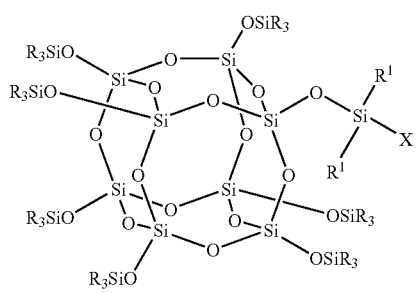
(1)

Herein X is a polymerizable group of 1 to 40 carbon atoms containing at least one oxygen atom; $R^1$ which may be the same or different is selected from among saturated hydrocarbon groups of 1 to 20 carbon atoms, aromatic hydrocarbon groups of 6 to 20 carbon atoms, organoxy groups of 1 to 20 carbon atoms, and halogen atoms; R is a non-polymerizable monovalent hydrocarbon group of 1 to 40 carbon atoms which may be substituted with one or more halogen atoms, and the R groups bonded to a common silicon atom may be the same or different.

In a second aspect, the invention provides a method for preparing a monofunctional monomer having a cage oligosiloxane structure, represented by the general formula (1), comprising reacting a cage oligosiloxane having a silanol site represented by the following general formula (2) with an organosilicon compound represented by the following general formula (3).

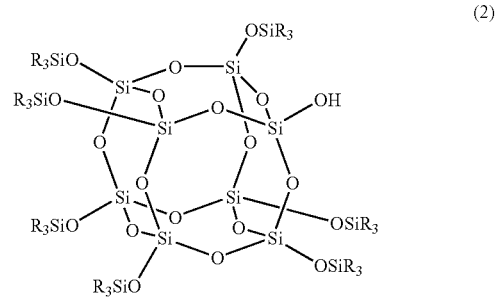
(2)

Herein R is a non-polymerizable monovalent hydrocarbon group of 1 to 40 carbon atoms which may be substituted with one or more halogen atoms, and the R groups bonded to a common silicon atom may be the same or different.

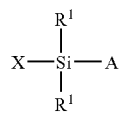
(3)

Herein X is a polymerizable group of 1 to 40 carbon atoms containing at least one oxygen atom, A is an organoxy group of 1 to 20 carbon atoms or a halogen atom, and $R^1$ which may be the same or different is selected from among saturated hydrocarbon groups of 1 to 20 carbon atoms, aromatic hydrocarbon groups of 6 to 20 carbon atoms, organoxy groups of 1 to 20 carbon atoms, and halogen atoms.

In another embodiment, the invention provides a method for preparing a monofunctional monomer having a cage oligosiloxane structure, represented by the general formula (1), comprising the steps of reacting a cage oligosiloxane having a silanol site represented by the following general formula (2) with an organosilicon compound represented by the following general formula (4), and combining the reaction product with an unsaturated compound of up to 40 carbon atoms having at least one oxygen atom-containing polymerizable group represented by the following general formula (5) through hydrosilylation reaction.

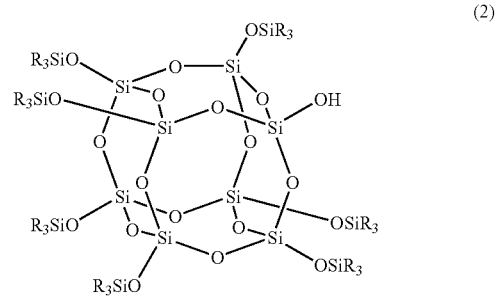
(2)

Herein R is a non-polymerizable monovalent hydrocarbon group of 1 to 40 carbon atoms which may be substituted with one or more halogen atoms, and the R groups bonded to a common silicon atom may be the same or different.

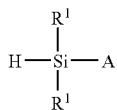

(4)

Herein A is an organoxy group of 1 to 20 carbon atoms or a halogen atom. $R^1$ which may be the same or different is selected from among saturated hydrocarbon groups of 1 to 20 carbon atoms, aromatic hydrocarbon groups of 6 to 20 carbon atoms, organoxy groups of 1 to 20 carbon atoms, and halogen atoms.

(5)

Herein Z is a polymerizable monovalent organic group of 1 to 38 carbon atoms containing at least one oxygen atom.

According to the present invention, a novel monofunctional monomer with a cage oligosiloxane structure having improved compatibility with solvents and other polymerizable monomers is available as well as a method for preparing the same. With the method of the invention, a monofunctional monomer with a cage oligosiloxane structure can be prepared in one stage, in high yields and in high purity.

DESCRIPTION OF THE PREFERRED EMBODIMENTS

The monofunctional monomer having a cage oligosiloxane structure according to the present invention is represented by the following general formula (1).

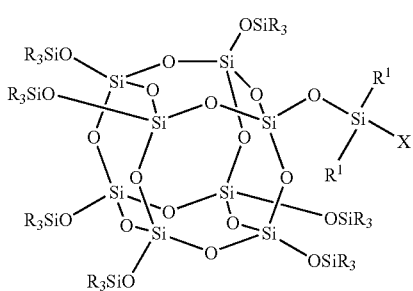

(1)

In formula (1), X is a polymerizable group of 1 to 40 carbon atoms containing at least one oxygen atom. Examples include cyclic ether-containing groups such as oxiranyl, 2,3-epoxypropyl, 3,4-epoxybutyl, 3,4-epoxycyclohexyl, 2,3-epoxycyclohexyl, glycidyloxypropyl, 3,4-epoxycyclohexylethyl, 3-ethyloxetan-3-ylmethyl, and [3-(3-ethyloxetan-3-yl)methyloxy]propyl; (meth)acryloyl-containing groups such as acryloyloxypropyl, acryloyloxymethyl, methacryloyloxypropyl, methacryloyloxymethyl, acryloylaminomethyl, acryloylaminopropyl, methacryloylaminomethyl, methacryloylaminopropyl, acryloylthiopropyl, and methacryloylthiopropyl; cyclic acid anhydride-containing groups such as tetrahydrofuran-2,5-dion-3-ylpropyl and 1,3-dihydroisobenzofuran-1,3-dion-5-yl; and vinyl ether-containing groups such as vinyloxymethyl, vinyloxypropyl, isopropenoxymethyl and isopropenoxypropyl. In particular, the inclusion of methacryloyl groups, acryloyl groups, epoxides and cyclic acid anhydrides is preferred.

In formula (1), $R^1$ may be the same or different and is selected from among saturated hydrocarbon groups of 1 to 20 carbon atoms, aromatic hydrocarbon groups of 6 to 20 carbon atoms, organoxy groups of 1 to 20 carbon atoms, and halogen atoms. Examples of $R^1$ include straight, branched or cyclic alkyl groups such as methyl, ethyl, n-propyl, isopropyl, n-butyl, isobutyl, tert-butyl, pentyl, cyclopentyl, isopentyl, tert-pentyl, hexyl, cyclohexyl, 2-ethylhexyl, octyl, isooctyl, decyl, dodecyl, and stearyl; aryl groups such as phenyl, 4-tert-butylphenyl, 2-tolyl, 3-tolyl, 4-tolyl, 2,6-dimethylphenyl, 2,4-dimethylphenyl, 3,5-dimethylphenyl, 3,4-dimethylphenyl, 2,5-dimethylphenyl, naphthyl, and biphenylyl; aralkyl groups such as benzyl, 1-phenylethyl, 2-phenylethyl, and naphthylethyl; organoxy groups such as methoxy, ethoxy, n-propoxy, isopropoxy, n-butoxy, isobutoxy, tert-butoxy, pentyloxy, cyclopentyloxy, isopentyloxy, tert-pentyloxy, hexyloxy, cyclohexyloxy, 2-ethylhexyloxy, octyloxy, isooctyloxy, decyloxy, dodecyloxy, stearyloxy, phenoxy, 4-tert-butylphenoxy, 2-tolyloxy, 3-tolyloxy, 4-tolyloxy, 2,6-dimethylphenoxy, 2,4-dimethylphenoxy, 3,5-dimethylphenoxy, 3,4-dimethylphenoxy, 2,5-dimethylphenoxy, naphthyloxy, biphenylyloxy, benzyloxy, and phenylethyloxy; and fluoro, chloro, bromo and iodo.

In formula (1), R is a non-polymerizable monovalent hydrocarbon group of 1 to 40 carbon atoms which may be substituted with one or more halogen atoms, and the R groups bonded to a common silicon atom may be the same or different. Examples of R include straight, branched or cyclic alkyl groups such as methyl, chloromethyl, ethyl, n-propyl, isopropyl, n-butyl, isobutyl, tert-butyl, pentyl, cyclopentyl, isopentyl, tert-pentyl, hexyl, cyclohexyl, 4-tert-butylcyclohexyl, 2-ethylhexyl, octyl, isooctyl, decyl, dodecyl, stearyl, hexadecyl, octadecyl, and eicosyl; aryl groups such as phenyl, 4-tert-butylphenyl, 3,5-di-tert-butylphenyl, 2-tolyl, 3-tolyl, 4-tolyl, 2,6-dimethylphenyl, 2,4-dimethylphenyl, 3,5-dimethylphenyl, 3,4-dimethylphenyl, 2,5-dimethylphenyl, naphthyl, biphenylyl, phenanthryl, and anthracenyl; and aralkyl groups such as benzyl, 1-phenylethyl, 2-phenylethyl and naphthylethyl.

Examples of the monofunctional monomer having a cage oligosiloxane structure represented by the general formula (1) include 1-oxiranyldimethylsiloxy-3,5,7,9,11,13,15-heptakis-(trimethylsiloxy)pentacyclo[9.5.1.1$^{3,9}$.1$^{5,5}$.1$^{7,13}$]octasiloxane, 1-(2,3-epoxypropyl)dimethylsiloxy-3,5,7,9,11,13,15-heptakis-(trimethylsiloxy)pentacyclo[9.5.1.1$^{3,9}$.1$^{5,15}$.1$^{7,13}$]octasiloxane, 1-(3,4-epoxycyclohexyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(2,3-epoxycyclohexyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(glycidyloxypropyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3,4-epoxycyclohexylethyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(2,3-epoxycyclohexylethyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-[3-(3-ethyloxetan-3-yl)methyloxy]propyldimethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(acryloyloxymethyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-[(3-methacryloyloxy)propyl]dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(methacryloyloxymethyl)dimethylsiloxy-3,5,7,9,11,13,15-heptakis(trimethylsiloxy)pentacyclo[9.5.1.1$_{3,9}$.1$^{5,15}$.1$^{7,13}$]-octasiloxane, 1-(acryloylaminomethyl)dimethylsiloxy-3,5,7,9,11,13,15-heptakis(trimethylsiloxy)pentacyclo[9.5.1.1$^{3,9}$.1$^{5,15}$.1$^{7,13}$]octasiloxane, 1-[(3-acryloylamino)propyl]dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(methacryloylaminomethyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-[3-(methacryloylamino)propyl]dimethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-[3-(acryloylthio)propyl]dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-[3-(methacryloylthio)propyl]dimethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(vinyloxymethyl)dimethylsiloxy-3,5,7,9,11,13,15-heptakis-(trimethylsiloxy)pentacyclo[9.5.1.1$^{3,9}$.1$^{5,15}$.1$^{7,13}$]octasiloxane, 1-(vinyloxypropyl)dimethylsiloxy-3,5,7,9,11,13,15-heptakis-(trimethylsiloxy)pentacyclo[9.5.1.1$^{3,9}$.1$^{5,15}$.1$^{7,13}$]octasiloxane, 1-(isopropenoxymethyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(isopropenoxypropyl)dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(glycidyloxypropyl)diethylsiloxy-3,5,7,9,11,13,15-heptakis-(trimethylsiloxy)pentacyclo[9.5.1.1$^{3,9}$.1$^{5,15}$.1$^{7,13}$]octasiloxane, 1-(3,4-epoxycyclohexylethyl)diethylsiloxy-3,5,7,9,11,13,15-heptakis(trimethylsiloxy)pentacyclo[9.5.1.1$^{3,5}$.1$^{5,15}$.1$^{7,13}$]-octasiloxane, 1-(3-acryloyloxypropyl)diethylsiloxy-3,5,7,9,11,13,15-heptakis(trimethylsiloxy)pentacyclo[9.5.1.1$^{3,9}$.1$^{5,15}$.1$^{7,13}$]octasiloxane, 1-(3-methacryloyloxypropyl)diethylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(tetrahydrofuran-2,5-dion-3-ylpropyl)diethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)diethylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(glycidyloxypropyl)(methoxy)methylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3,4-epoxycyclohexylethyl)(methoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(3-acryloyloxypropyl)(methoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(3-methacryloyloxypropyl)(methoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)(methoxy)methylsiloxy-3,5,7,9,11,13,15-heptakis(trimethylsiloxy)pentacyclo-[9.5.1.1$^{3,9}$.1$^{5,15}$1$^{7,13}$]octasiloxane, 1-(1,3-dihydroisobenzofuran-1,3-dion-5-yl)(methoxy)-methylsiloxy-3,5,7,9,11,13,15-heptakis(trimethylsiloxy)-pentacyclo[9.5.1.1$^{3,9}$.1$^{5,15}$.1$^{7,13}$]octasiloxane, 1-(glycidyloxypropyl)dimethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3,4-epoxycyclohexylethyl)dimethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3-acryloyloxypropyl)dimethoxysiloxy-3,5,7,9,11,13,15-heptakis(trimethylsiloxy)pentacyclo[9.5.1.1$^{3,9}$.1$^{5,1}$.1$^{7,13}$]-octasiloxane, 1-(3-methacryloyloxypropyl)dimethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(tetrahydrofuran-2,5-dion-3-ylpropyl)dimethoxysiloxy-3,5,7,9,11,13,15-heptakis(trimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)dimethoxysiloxy-3,5,7,9,11,13,15-heptakis(trimethylsiloxy)pentacyclo-[9.5.1.1$^{3,9}$.1$^{5,15}$.1$^{7,13}$]octasiloxane, 1-(glycidyloxypropyl)(ethoxy)methylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3,4-epoxycyclohexylethyl)(ethoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(3-acryloyloxypropyl)(ethoxy)methylsiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3-methacryloyloxypropyl)(ethoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)(ethoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)(ethoxy)methylsiloxy-3,5,7,9,11,13,15-heptakis(trimethylsiloxy)pentacyclo-[9.5.1.1$^{3,9}$.1$^{5,15}$.1$^{7,13}$]octasiloxane, 1-(glycidyloxypropyl)diethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3,4-epoxycyclohexylethyl)diethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3-acryloyloxypropyl)diethoxysiloxy-3,5,7,9,11,13,15-heptakis(trimethylsiloxy)pentacyclo[9.5.1.1$^{3,9}$.1$^{5,15}$.1$^{7,13}$]-octasiloxane, 1-(3-methacryloyloxypropyl)diethoxysiloxy-3,5,7,9,11,13, 15-heptakis(trimethylsiloxy)pentacyclo[9.5.1.1$^{3,9}$. 1$^{5,15}$.1$^{7,13}$]-octasiloxane, 1-(tetrahydrofuran-2,5-dion-3-ylpropyl)diethoxysiloxy-3,5, 7,9,11,13,15-heptakis(trimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)diethoxysiloxy-3,5,7,9,11,13,15-heptakis(trimethylsiloxy)pentacyclo-[9.5.1.1$^{3,9}$.1$^{5,15}$.1$^{7,13}$]octasiloxane, 1-(glycidyloxypropyl)dimethylsiloxy-3,5,7,9,11,13,15-heptakis(ethyldimethylsiloxy)pentacyclo[9.5.1.1$^{3,9}$.1$^{5,15}$.1$^{7,13}$]-octasiloxane, 1-(3,4-epoxycyclohexylethyl)dimethylsiloxy-3,5,7,9,11,13, 15-heptakis(ethyldimethylsiloxy)pentacyclo[9.5.1.1$^{3,9}$.1$^{5,15}$.1$^{7,13}$]-octasiloxane, 1-(3-acryloyloxypropyl)dimethylsiloxy-3,5,7,9,11,13,15-heptakis(ethyldimethylsiloxy)pentacyclo[9.5.1.1$^{3,9}$.1$^{5,15}$.1$^{7,13}$]-octasiloxane, 1-(3-methacryloyloxypropyl)dimethylsiloxy-3,5,7,9,11,13, 15-heptakis(ethyldimethylsiloxy)pentacyclo[9.5.1.1$^{3,9}$.1$^{5,15}$.1$^{7,13}$]-octasiloxane, 1-(tetrahydrofuran-2,5-dion-3-ylpropyl)dimethylsiloxy-3,5, 7,9,11,13,15-heptakis(ethyldimethylsiloxy)pentacyclo-[9.5.1.1$^{3,9}$.1$^{5,15}$.1$^{7,13}$)]octasiloxane, 1-(1,3-dihydroisobenzofuran-1,3-dion-5-yl)dimethylsiloxy-3,5,7,9,11,13,15-heptakis(ethyldimethylsiloxy)pentacyclo-[9.5.1.1$^{3,9}$.1$^{5,15}$.1$^{7,13}$-octasiloxane, 1-(glycidyloxypropyl)dimethylsiloxy-3,5,7,9,11,13,15-heptakis(triethylsiloxy)pentacyclo[9.5.1.1$^{3,9}$.1$^{5,15}$.1$^{7,13}$]-octasiloxane, 1-(3,4-epoxycyclohexylethyl)dimethylsiloxy-3,5,7,9,11,13, 15-heptakis(triethylsiloxy)pentacyclo[9.5.1.1$^{3,9}$.1$^{5,15}$.1$^{7,13}$]-octasiloxane, 1-(3-acryloyloxypropyl)dimethylsiloxy-3,5,7,9,11,13,15-heptakis(triethylsiloxy)pentacyclo[9.5.1.1$^{3,9}$.1$^{5,15}$.1$^{7,13}$]-octasiloxane, 1-(3-methacryloyloxypropyl)dimethylsiloxy-3,5,7,9,11,13, 15-heptakis(triethylsiloxy)pentacyclo[9.5.1.1$^{3,9}$.1$^{5,15}$.1$^{7,13}$]-octasiloxane, 1-(tetrahydrofuran-2,5-dion-3-ylpropyl)dimethylsiloxy-3,5, 7,9,11,13,15-heptakis(triethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis(triethylsiloxy)pentacyclo-[9.5.1.1$^{3,9}$.1$^{5,15}$.1$^{7,13}$]octasiloxane, 1-(glycidyloxypropyl)dimethylsiloxy-3,5,7,9,11,13,15-heptakis(phenyldimethylsiloxy)pentacyclo[9.5.1.1$^{3,9}$.1$^{5,15}$.1$^{7,13}$]-octasiloxane, 1-(3,4-epoxycyclohexylethyl)dimethylsiloxy-3,5,7,9,11,13, 15-heptakis(phenyldimethylsiloxy)pentacyclo[9.5.1.1$^{3,9}$.1$^{5,15}$.1$^{7,13}$]-octasiloxane, 1-(3-acryloyloxypropyl)dimethylsiloxy-3,5,7,9,11,13,15-heptakis(phenyldimethylsiloxy)pentacyclo[9.5.1.1$^{3,9}$.1$^{5,15}$.1$^{7,13}$]-octasiloxane, 1-(3-methacryloyloxypropyl)dimethylsiloxy-3,5,7,9,11,13, 15-heptakis(phenyldimethylsiloxy)pentacyclo[9.5.1.1$^{3,9}$.1$^{5,15}$.1$^{7,13}$]-octasiloxane, 1-(tetrahydrofuran-2,5-dion-3-ylpropyl)dimethylsiloxy-3,5, 7,9,11,13,15-heptakis(phenyldimethylsiloxy)pentacyclo-[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis(phenyldimethylsiloxy)pentacyclo-[9.5.1.1$^{3,9}$.1$^{5,15}$.1$^{7,13}$]octasiloxane, 1-(glycidyloxypropyl)dimethylsiloxy-3,5,7,9,11,13,15-heptakis(tert-butyldimethylsiloxy)pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13, 15-heptakis(tert-butyldimethylsiloxy)pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis(tert-butyldimethylsiloxy)pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13, 15-heptakis(tert-butyldimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5, 7,9,11,13,15-heptakis(tert-butyldimethylsiloxy)-pentacyclo[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis(tert-butyldimethylsiloxy)-pentacyclo[9.5.1.1$^{3,9}$.1$^{5,15}$.1$^{7,13}$]octasiloxane, 1-(glycidyloxypropyl)dimethylsiloxy-3,5,7,9,11,13,15-heptakis(chloromethyldimethylsiloxy)pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13, 15-heptakis(chloromethyldimethylsiloxy)pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis(chloromethyldimethylsiloxy)pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13, 15-heptakis(chloromethyldimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5, 7,9,11,13,15-heptakis(chloromethyldimethylsiloxy)-pentacyclo[9.5.1.1$^{3,9}$. 1$^{5,15}$.1$^{7,13}$]octasiloxane, 1-(1,3-dihydroisobenzofuran-1,3-dion-5-yl)dimethylsiloxy-3,5,7,9,11,13,15-heptakis(chloromethyldimethylsiloxy)-pentacyclo[9.5.1.1$^{3,9}$.1$^{5,15}$.1$^{7,13}$]octasiloxane, 1-(glycidyloxypropyl)dimethylsiloxy-3,5,7,9,11,13,15-heptakis[(3-chloropropyl)dimethylsiloxy]pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13, 15-heptakis[(3-chloropropyl)dimethylsiloxy]pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis[(3-chloropropyl)dimethylsiloxy]pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13, 15-heptakis[(3-chloropropyl)dimethylsiloxy]pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5, 7,9,11,13,15-heptakis[(3-chloropropyl)dimethylsiloxy]-pentacyclo[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis[(3-chloropropyl)dimethylsiloxy]-pentacyclo[9.5.1.1$^{3,9}$.1$^{5,15}$.1$^{7,13}$]octasiloxane, 1-(glycidyloxypropyl)dimethylsiloxy-3,5,7,9,11,13,15-heptakis(3,3,3-trifluoropropyldimethylsiloxy)pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13, 15-heptakis(3,3,3-trifluoropropyldimethylsiloxy)pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis(3,3,3-trifluoropropyldimethylsiloxy)pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13, 15-heptakis(3,3,3-trifluoropropyldimethylsiloxy)pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5, 7,9,11,13,15-heptakis(3,3,3-trifluoropropyldimethyl-siloxy)pentacyclo[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis(3,3,3-trifluoropropyldimethylsiloxy)pentacyclo[9.5.1.1$^{3,9}$.1$^{5,15}$.1$^{7,13}$]octasiloxane, 1-(glycidyloxypropyl)dimethylsiloxy-3,5,7,9,11,13,15-heptakis[(nonafluorohexyl)dimethylsiloxy]pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13,15-heptakis[(nonafluorohexyl)dimethylsiloxy]pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis[(nonafluorohexyl)dimethylsiloxy]pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13,15-heptakis[(nonafluorohexyl)dimethylsiloxy]pentacyclo-[9.5.1.1$^{3,9}$.1$^{1,15}$.1$^{7,13}$]octasiloxane, 1-(tetrahydrofuran-2,5-dion-3-ylpropyl)dimethylsiloxy-3,5,7,9,11,13,15-heptakis[(nonafluorohexyl)dimethylsiloxy]-pentacyclo[9.5.1.1$^{3,9}$.1$^{5,15}$.1$^{7,13}$]octasiloxane, 1-(1,3-dihydroisobenzofuran-1,3-dion-5-yl)dimethylsiloxy-3,5,7,9,11,13,15-heptakis[(nonafluorohexyl)dimethylsiloxy]-pentacyclo[9.5.1.1$^{3,9}$.1$^{5,15}$.1$^{7,13}$]octasiloxane, 1-(glycidyloxypropyl)dimethylsiloxy-3,5,7,9,11,13,15-heptakis[(heptadecafluorodecyl)dimethylsiloxy]pentacyclo-[9.5.1.1$^{3,9}$.1$^{5,15}$.1$^{7,13}$]octasiloxane, 1-(3,4-epoxycyclohexylethyl)dimethylsiloxy-3,5,7,9,11,13,15-heptakis[(heptadecafluorodecyl)dimethylsiloxy]pentacyclo-[9.5.1.1$^{3,9}$.1$^{5,15}$.1$^{7,13}$]octasiloxane, 1-(3-acryloyloxypropyl)dimethylsiloxy-3,5,7,9,11,13,15-heptakis[(heptadecafluorodecyl)dimethylsiloxy]pentacyclo-[9.5.1.1$^{3,9}$.1$^{5,15}$.1$^{7,13}$]octasiloxane, 1-(3-methacryloyloxypropyl)dimethylsiloxy-3,5,7,9,11,13,15-heptakis[(heptadecafluorodecyl)dimethylsiloxy]pentacyclo-[9.5.1.1$^{3,9}$.1$^{5,15}$.1$^{7,13}$]octasiloxane, 1-(tetrahydrofuran-2,5-dion-3-ylpropyl)dimethylsiloxy-3,5,7,9,11,13,15-heptakis[(heptadecafluorodecyl)dimethylsiloxy]pentacyclo[9.5.1.1$^{3,9}$.1$^{1,15}$.1$^{7,13}$]octasiloxane, 1-(1,3-dihydroisobenzofuran-1,3-dion-5-yl)dimethylsiloxy-3,5,7,9,11,13,15-heptakis[(heptadecafluorodecyl)dimethylsiloxy]pentacyclo[9.5.1.1$^{3,9}$.1$^{5,15}$.1$^{7,13}$]octasiloxane, etc.

The present invention also provides a method for preparing a monofunctional monomer having a cage oligosiloxane structure, represented by the general formula (1). According to the invention, the monofunctional monomer having a cage oligosiloxane structure represented by formula (1) is prepared by reacting a cage oligosiloxane having a silanol site represented by the following general formula (2) with an organosilicon compound represented by the following general formula (3).

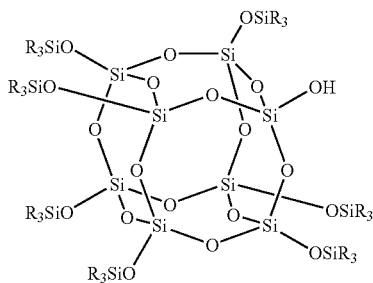

(2)

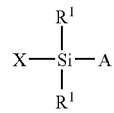

(3)

In formula (2), R is a substituent group as defined in formula (1).

It is reported, for example, by Hasegawa et al. that the compounds of formula (2) are formed through reaction of tetramethylammonium silicate with triorganochlorosilanes (see Synthesis and Reactivity in Inorganic and Metal-Organic Chemistry, 1994, vol. 24, pp. 1099-1110).

In formula (3), X and R$^1$ are substituent groups as defined in formula (1). A is an organoxy group of 1 to 20 carbon atoms or a halogen atom. Examples of the substituent group A include organoxy groups such as methoxy, methoxymethoxy, ethoxy, methoxyethoxy, ethoxyethoxy, n-propoxy, isopropoxy, n-butoxy, isobutoxy, tert-butoxy, pentyloxy, cyclopentyloxy, isopentyloxy, tert-pentyloxy, hexyloxy, cyclohexyloxy, 2-ethylhexyloxy, octyloxy, isooctyloxy, decyloxy, dodecyloxy, stearyloxy, tetradecyloxy, hexadecyloxy, ocatadecyloxy, eicosyloxy, phenoxy, 4-tert-butylphenoxy, 2-tolyloxy, 3-tolyloxy, 4-tolyloxy, 2,6-dimethylphenoxy, 2,4-dimethylphenoxy, 3,5-dimethylphenoxy, 3,4-dimethylphenoxy, 2,5-dimethylphenoxy, naphthyloxy, biphenylyloxy, benzyloxy, and phenylethyloxy; and fluoro, chloro, bromo and iodo.

Examples of the compound of formula (3) include
oxiranyldimethylmethoxysilane, oxiranyldimethylethoxysilane, oxiranyldimethylisopropoxysilane, oxiranylmethyldimethoxysilane, oxiranylmethyldiethoxysilane, oxiranyltrimethoxysilane, and oxiranyltriethoxysilane;

(2,3-epoxypropyl)dimethylmethoxysilane, (2,3-epoxypropyl)dimethylethoxysilane, (2,3-epoxypropyl)dimethylisopropoxysilane, (2,3-epoxypropyl)methyldimethoxysilane, (2,3-epoxypropyl)methyldiethoxysilane, (2,3-epoxypropyl)trimethoxysilane, and (2,3-epoxypropyl)triethoxysilane;

(3,4-epoxycyclohexyl)dimethylmethoxysilane, (3,4-epoxycyclohexyl)dimethylethoxysilane, (3,4-epoxycyclohexyl)dimethylisopropoxysilane, (3,4-epoxycyclohexyl)methyldimethoxysilane, (3,4-epoxycyclohexyl)methyldiethoxysilane, (3,4-epoxycyclohexyl)trimethoxysilane, and (3,4-epoxycyclohexyl)triethoxysilane;

(2,3-epoxycyclohexyl)dimethylmethoxysilane, (2,3-epoxycyclohexyl)dimethylethoxysilane, (2,3-epoxycyclohexyl)dimethylisopropoxysilane, (2,3-epoxycyclohexyl)methyldimethoxysilane, (2,3-epoxycyclohexyl)methyldiethoxysilane, (2,3-epoxycyclohexyl)trimethoxysilane, and (2,3-epoxycyclohexyl)triethoxysilane;

(glycidyloxypropyl)dimethylmethoxysilane, (glycidyloxypropyl)dimethylethoxysilane, (glycidyloxypropyl)dimethylisopropoxysilane, (glycidyloxypropyl)methyldimethoxysilane, (glycidyloxypropyl)methyldiethoxysilane, (glycidyloxypropyl)trimethoxysilane, and (glycidyloxypropyl)triethoxysilane;

(3,4-epoxycyclohexylethyl)dimethylmethoxysilane, (3,4-epoxycyclohexylethyl)dimethylethoxysilane, (3,4-epoxycyclohexylethyl)dimethylisopropoxysilane, (3,4-epoxycyclohexylethyl)methyldimethoxysilane, (3,4-epoxycyclohexylethyl)methyldiethoxysilane, (3,4-epoxycyclohexylethyl)trimethoxysilane, and (3,4-epoxycyclohexylethyl)triethoxysilane;

oxetanyldimethylmethoxysilane, oxetanyldimethylethoxysilane, oxetanyldimethylisopropoxysilane, oxetanylmethyldimethoxysilane, oxetanylmethyldiethoxysilane, oxetanyltrimethoxysilane, and oxetanyltriethoxysilane;

acryloyloxypropyldimethylchlorosilane, acryloyloxypropyldimethylbromosilane, acryloyloxypropyldimethyliodosilane, acryloyloxypropyldimethylfluorosilane, acryloyloxypropylmethyldichlorosilane, acryloyloxypropyltrichlorosilane, acryloyloxypropyldimethylmethoxysilane, acryloyloxypropyldimethylethoxysilane, acryloyloxypropyldimethylisopropoxysilane, acryloyloxypropylmethyldimethoxysilane, acryloyloxypropylmethyldiethoxysilane, acryloyloxypropyltrimethoxysilane, acryloyloxypropyltriethoxysilane, methacryloyloxypropyldimethylchlorosilane, methacryloyloxypropyldimethylbromosilane, methacryloyloxypropyldimethyliodosilane, methacryloyloxypropyldimethylfluorosilane, methacryloyloxypropylmethyldichlorosilane, methacryloyloxypropyltrichlorosilane, methacryloyloxypropyldimethylmethoxysilane, methacryloyloxypropyldimethylethoxysilane, methacryloyloxypropyldimethylisopropoxysilane, methacryloyloxypropylmethyldimethoxysilane, methacryloyloxypropylmethyldiethoxysilane, methacryloyloxypropyltrimethoxysilane, methacryloyloxypropyltriethoxysilane, (tetrahydrofuran-2,5-dion-3-ylpropyl)dimethylchlorosilane, (tetrahydrofuran-2,5-dion-3-ylpropyl)dimethylbromosilane, (tetrahydrofuran-2,5-dion-3-ylpropyl)dimethyliodosilane, (tetrahydrofuran-2,5-dion-3-ylpropyl)dimethylfluorosilane, (tetrahydrofuran-2,5-dion-3-ylpropyl)methyldichlorosilane, (tetrahydrofuran-2,5-dion-3-ylpropyl)trichlorosilane, (tetrahydrofuran-2,5-dion-3-ylpropyl)dimethylmethoxysilane, (tetrahydrofuran-2,5-dion-3-ylpropyl)dimethylethoxysilane, (tetrahydrofuran-2,5-dion-3-ylpropyl)dimethylisopropoxysilane, (tetrahydrofuran-2,5-dion-3-ylpropyl)methyldimethoxysilane, (tetrahydrofuran-2,5-dion-3-ylpropyl)methyldiethoxysilane, (tetrahydrofuran-2,5-dion-3-ylpropyl)trimethoxysilane, (tetrahydrofuran-2,5-dion-3-ylpropyl)triethoxysilane, (1,3-dihydroisobenzofuran-1,3-dion-5-yl)dimethylchlorosilane, (1,3-dihydroisobenzofuran-1,3-dion-5-yl)dimethylbromosilane, (1,3-dihydroisobenzofuran-1,3-dion-5-yl)dimethyliodosilane, (1,3-dihydroisobenzofuran-1,3-dion-5-yl)dimethylfluorosilane, (1,3-dihydroisobenzofuran-1,3-dion-5-yl)methyldichlorosilane, (1,3-dihydroisobenzofuran-1,3-dion-5-yl)trichlorosilane, (1,3-dihydroisobenzofuran-1,3-dion-5-yl)dimethylmethoxysilane, (1,3-dihydroisobenzofuran-1,3-dion-5-yl)dimethylethoxysilane, (1,3-dihydroisobenzofuran-1,3-dion-5-yl)dimethylisopropoxysilane, (1,3-dihydroisobenzofuran-1,3-dion-5-yl)methyldimethoxysilane, (1,3-dihydroisobenzofuran-1,3-dion-5-yl)methyldiethoxysilane, (1,3-dihydroisobenzofuran-1,3-dion-5-yl)trimethoxysilane, (1,3-dihydroisobenzofuran-1,3-dion-5-yl)triethoxysilane, etc.

In the method of the invention, the monofunctional monomer having a cage oligosiloxane structure represented by formula (1) is prepared by reacting a cage oligosiloxane having a silanol site represented by formula (2) with an organosilicon compound represented by formula (3). Although the molar ratio of compound of formula (2) to compound of formula (3) used in this reaction is theoretically 1:1, either one of the compounds may be used in excess.

In the reaction, an acid or base is preferably used as a catalyst or promoter. Examples of the acid which can be used herein include hydrochloric acid, hydrobromic acid, hydroiodic acid, phosphoric acid, sulfuric acid, acetic acid, propionic acid, trifluoroacetic acid, methanesulfonic acid, benzenesulfonic acid, p-toluenesulfonic acid, dodecylbenzenesulfonic acid, and trifluoromethanesulfonic acid. The acid is generally used in an amount of 0.1 to 50 mol %.

Examples of the base which can be used herein include amines such as triethylamine, tributylamine, N-methylpiperidine, 1,4-diazabicyclo[2.2.2]octane, and N,N-dimethylaniline; nitrogen-containing heterocyclic compounds such as pyridine, N,N-dimethylaminopyridine, and 1,8-diazabicyclo[5.4.0]-7-undecene; and salts such as sodium acetate, potassium acetate, sodium carbonate, potassium carbonate, cesium carbonate, and potassium phosphate. The base is generally used in an amount of 0.1 to 50 mol % as a catalyst and in an amount of 1 to 1.5 equivalents as a promoter or acid trapping agent.

The reaction is typically performed under atmospheric pressure or reduced pressure and in an inert gas atmosphere such as nitrogen although the reaction conditions are not limited thereto. The reaction temperature is generally in the range of −20° C. to 100° C., preferably 0° C. to 60° C.

Preferably the reaction is performed in a solvent. Suitable solvents include hydrocarbons such as hexane, isooctane, benzene, toluene and xylene, halogenated hydrocarbons such as dichloromethane and dichloroethane, ethers such as diethyl ether and tetrahydrofuran, ketones such as acetone and methyl isobutyl ketone, amides such as N,N-dimethylacetamide, N,N-dimethylformamide, and N-methylpyrrolidone, nitriles such as acetonitrile and benzonitrile, and sulfur compounds such as dimethyl sulfoxide and sulfolane.

Optionally a polymerization inhibitor is added during the reaction. Typical polymerization inhibitors are hindered phenols such as 2,6-di-tert-butyl-4-methylphenol (BHT) and 1,3,5-tris(3,5-di-tert-butyl-4-hydroxybenzyl)-2,4,6-trimethylbenzene.

According to the invention, an alternative method for preparing the compound of formula (1) is provided. In the alternative embodiment, the monofunctional monomer having a cage oligosiloxane structure represented by formula (1) is prepared by reacting a cage oligosiloxane having a silanol site represented by the following general formula (2) with an organosilicon compound represented by the following general formula (4), and combining the reaction product with an unsaturated compound of up to 40 carbon atoms having at least one oxygen atom-containing polymerizable group represented by the following general formula (5) through hydrosilylation reaction.

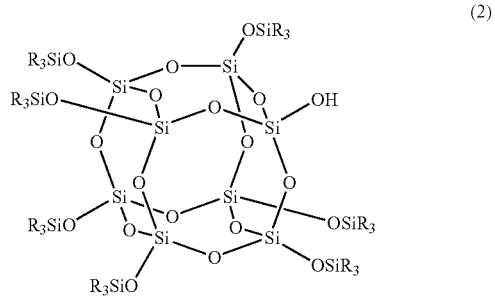

(2)

Herein R is a non-polymerizable monovalent hydrocarbon group of 1 to 40 carbon atoms which may be substituted with one or more halogen atoms, and the R groups bonded to a common silicon atom may be the same or different.

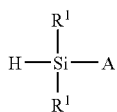
(4)

Herein A is an organoxy group of 1 to 20 carbon atoms or a halogen atom, and $R^1$ is independently selected from among saturated hydrocarbon groups of 1 to 20 carbon atoms, aromatic hydrocarbon groups of 6 to 20 carbon atoms, organoxy groups of 1 to 20 carbon atoms, and halogen atoms.

(5)

Herein Z is a polymerizable monovalent organic group of 1 to 38 carbon atoms containing at least one oxygen atom.

A and $R^1$ in formula (4) are the same substituent groups as A and $R^1$ in formula (3). The conditions under which the compounds of formulae (2) and (4) are reacted are the same as the above-described conditions under which the compounds of formulae (2) and (3) are reacted. The product resulting from the reaction of the compounds of formulae (2) and (4) is a cage oligosiloxane having an H—Si group. It is then combined with an unsaturated compound of formula (5) through hydrosilylation reaction, thereby obtaining a monofunctional monomer having a cage oligosiloxane structure, as defined by the invention. Examples of the unsaturated compound of formula (5) include cyclic ether-containing unsaturated compounds such as 3,4-epoxy-1-butene, allyl glycidyl ether, and 3,4-epoxy-1-vinylcyclohexene; (meth)acryloyl-containing unsaturated compounds such as allyl acrylate, allyl methacrylate, N-allylacrylamide, and N-allylmethacrylamide; and cyclic acid anhydride-containing unsaturated compounds such as allyl succinic acid anhydride; and vinyl ether-containing unsaturated compounds such as allyl vinyl ether.

Usually, the hydrosilylation reaction is performed in the presence of late-period transition metal catalysts, with platinum catalysts being preferred. Suitable platinum catalysts include chloroplatinic acid, platinum chloride, platinum black, platinum on activated carbon, platinum(0) tetramethyldivinyldisiloxane complex, platinum(0) tetramethyltetravinylcyclotetrasiloxane complex, tetrakis(triphenylphosphine) platinum(0), and dichloro(1,5-cyclooctadiene) platinum (II). An appropriate amount of the transition metal catalyst used is 0.00001 to 10 mol %, preferably 0.0001 to 1 mol % based on the moles of H—Si groups.

In the hydrosilylation reaction, a solvent may be used. Suitable solvents include hydrocarbons such as hexane, isooctane, toluene and xylene, and halogenated hydrocarbons such as methylene chloride, chloroform and dichloroethane. The reaction is typically performed in an inert gas atmosphere such as nitrogen or argon. In some cases, a minor amount of oxygen is introduced into the system for activating the catalyst. The reaction temperature is generally in the range of −20° C. to 200° C., preferably 0° C. to 150° C. After the completion of reaction, the desired monofunctional monomer having a cage oligosiloxane structure can be isolated by suitable techniques such as filtration, washing, adsorption, recrystallization and column chromatography.

EXAMPLE

Examples of the invention are given below by way of illustration and not by way of limitation. All reactions were performed in a nitrogen atmosphere.

Example 1

Synthesis of 1-[(3-methacryloyloxy)propyl]dimethylsiloxy-3,5,7,9,11,13,15-heptakis(trimethylsiloxy) pentacyclo-[9.5.1.1$^{3,9}$.1$^{5,15}$.1$^{7,13}$]octasiloxane

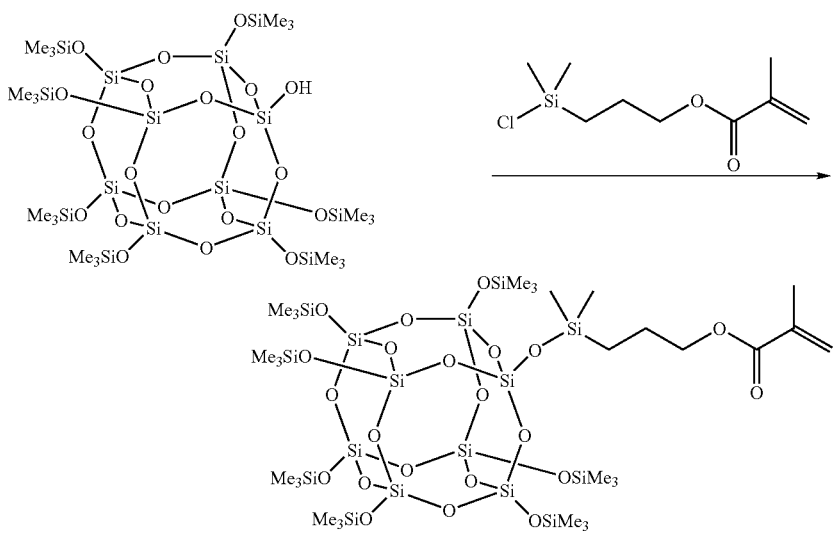

A 100-ml four-necked flask equipped with a Dimroth reflux condenser, stirrer, thermometer and rubber septum was purged with nitrogen. The flask was charged with 3.70 g (3.5 mmol) of 1-hydroxy-3,5,7,9,11,13,15-heptakis(trimethyl-siloxy)pentacyclo[9.5.1.1$^{3,9}$.1$^{5,15}$.1$^{7,13}$]octasiloxane in 33.3 g of toluene. To the flask, 1.06 g (4.8 mmol) of 3-(methacry- GPC (based on polystyrene standard, RI detector): $M_w$=1,295, $M_w/M_n$=1.005

Example 2

Synthesis of 1-[(3-glycidyloxy)propyl]dimethylsiloxy-3,5,7,9,11,13,15-heptakis(trimethylsiloxy)pentacyclo-[9.5.1.1$^{3,9}$.1$^{5,15}$.1$^{7,13}$]octasiloxane

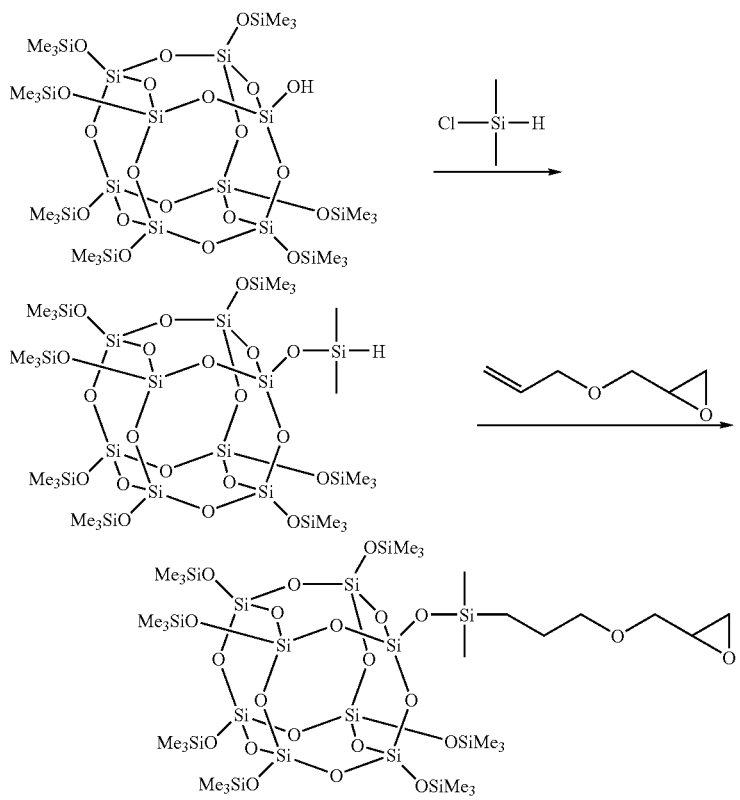

loyloxy)propyldimethylchlorosilane was added. With stirring at room temperature, 0.46 g (4.55 mmol) of triethylamine was slowly added dropwise using a micro-syringe through the rubber septum. After the completion of dropwise addition, stirring was continued for 13 hours at room temperature. Water, 10 ml, was added to the reaction mixture whereupon it separated into two layers. The organic layer was concentrated in vacuum. The crude product was washed three times with 5 ml of acetonitrile and dried in vacuum, leaving 3.72 g of the target compound as white solids. The yield was 86%. The results of identification by NMR, MALDI-TOFMS (matrix: cobalt) and GPC are shown below.

$^1$H-NMR (CDCl$_3$, 300 MHz): δ (ppm) 6.11-6.10 (1H, m), 5.54 (1H, quintet, J=1.7 Hz), 4.10 (1H, t, J=6.9 Hz), 1.95 (3H, s), 1.78-1.67 (2H, m), 0.66-0.60 (2H, m), 0.16 (6H, s), 0.15 (63H, s+s)

$^{13}$C-NMR (CDCl$_3$, 75.6 MHz): δ (ppm) 167.5, 136.6, 125.1, 67.1, 22.3, 18.3, 13.7, 1.2, −0.5

$^{29}$Si-NMR (CDCl$_3$, 59.7 MHz): δ (ppm) 12.6, 12.4, −108.8, −108.9, −109.0

MALDI-TOFMS: m/z 1263.4 (M+Na$^+$)

A 100-ml four-necked flask equipped with a Dimroth reflux condenser, stirrer, thermometer and rubber septum was purged with nitrogen. The flask was charged with 3.70 g (3.5 mmol) of 1-hydroxy-3,5,7,9,11,13,15-heptakis(trimethyl-siloxy)pentacyclo[9.5.1.1$^{3,9}$.1$^{5,15}$.1$^{7,13}$]octasiloxane in 33.3 g of toluene. To the flask, 0.47 g (5.0 mmol) of dimethylchlorosilane was added. With stirring at room temperature, 0.48 g (4.9 mmol) of triethylamine was slowly added dropwise using a micro-syringe through the rubber septum. After the completion of dropwise addition, stirring was continued for 10 hours at room temperature. Water, 10 ml, was added to the reaction mixture whereupon it separated into two layers. The organic layer was concentrated in vacuum. The crude product was washed three times with 5 ml of methanol and dried in vacuum, leaving 3.48 g of an intermediate compound, 1-dimethylsiloxy-3,5,7,9,11,13,15-heptakis(trimethylsiloxy)pentacyclo[9.5.1.1$^{3,9}$.1$^{5,15}$.1$^{7,13}$]-octasiloxane, as white solids. The yield was 89%.

Next, a 50-ml three-necked flask equipped with a Dimroth reflux condenser, stirrer and thermometer was purged with nitrogen. The flask was charged with 335 mg (0.30 mmol) of the 1-dimethylsiloxy-3,5,7,9,11,13,15-heptakis(trimethyl-siloxy)pentacyclo[9.5.1.1$^{3,9}$.1$^{5,15}$.1$^{7,13}$]octasiloxane obtained above and 51 mg (0.45 mmol) of allyl glycidyl ether in 3 ml of toluene. Then 0.2 mg of a toluene solution of platinum(0) divinyltetramethyldisiloxane complex (platinum 3 wt %) was added, followed by 10 hours of stirring at room temperature. The reaction mixture was concentrated in vacuum. The crude product was washed two times with 3 ml of methanol and dried in vacuum, leaving 325 mg of 1-[(3-glycidyloxy)propyl]-dimethylsiloxy-3,5,7,9,11,13,15-heptakis(trimethylsiloxy)-pentacyclo[9.5.1.1$^{3,9}$.1$^{5,15}$.1$^{7,13}$]octasiloxane as white solids. The yield was 88%. The results of identification by NMR, MALDI-TOFMS (matrix: cobalt) and GPC are shown below.

$^1$H-NMR (CDCl$_3$, 300 MHz): δ (ppm) 3.68 (1H, dd, J=11.4 Hz, 3.3 Hz), 3.52-3.42 (2H, m), 3.40 (1H, dd, J=11.4 Hz, 5.7 Hz), 3.17-3.11 (1H, m), 2.79 (1H, dd, J=5.1 Hz, 4.1 Hz), 2.61 (1H, dd, J=5.1 Hz, 2.8 Hz), 1.70-1.59 (2H, m), 0.64-0.58 (2H, m), 0.15+0.14 (69H, s+s)

$^{13}$C-NMR (CDCl$_3$, 75.6 MHz): δ (ppm) 74.2, 71.4, 50.8, 44.4, 23.2, 13.7, 1.3, 1.2, −0.4

$^{29}$Si-NMR (CDCl$_3$, 59.7 MHz): δ (ppm) 12.8, 12.6, −108.9

MALDI-TOFMS: m/z 1251.7 (M+Na$^+$)

GPC (based on polystyrene standard, RI detector):
$M_w$=1,273, $M_w/M_n$=1.005

Example 3

Synthesis of 1-[2-(3,4-epoxycyclohexyl)ethyl]dimethyl-siloxy-3,5,7,9,11,13,15-heptakis(trimethylsiloxy)-pentacyclo[9.5.1.1$^{3,9}$.1$^{5,15}$.1$^{7,13}$]octasiloxane

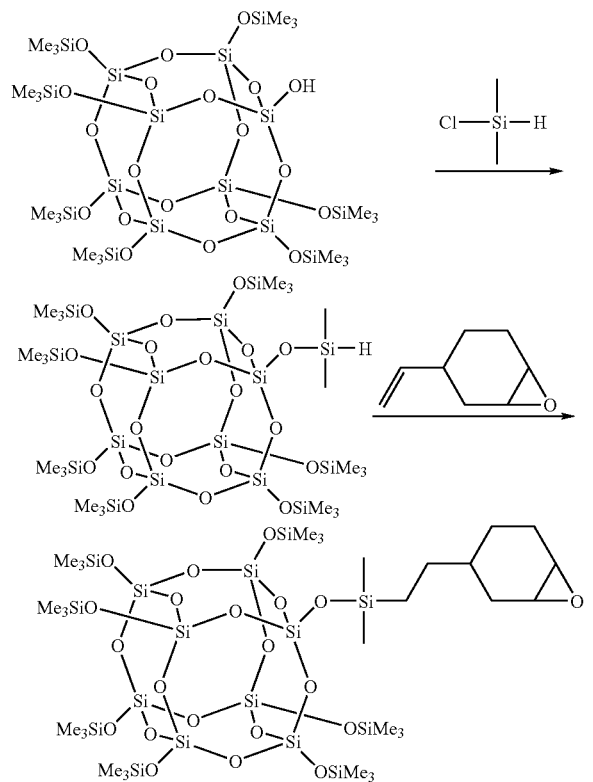

A 50-ml three-necked flask equipped with a Dimroth reflux condenser, stirrer and thermometer was purged with nitrogen. The flask was charged with 335 mg (0.30 mmol) of the intermediate compound, 1-dimethylsiloxy-3,5,7,9,11,13,15-heptakis(trimethylsiloxy)pentacyclo[9.5.1.1$^{3,9}$.1$^{5,15}$.1$^{7,13}$]-octasiloxane synthesized as in Example 2 and 45 mg (0.36 mmol) of 4-vinylcyclohexene oxide in 3 ml of toluene. Then 0.2 mg of a toluene solution of platinum(0) divinyltetramethyldisiloxane complex (platinum 3 wt %) was added, followed by 2 hours of stirring at room temperature. The reaction mixture was concentrated in vacuum. The crude product was washed three times with 2 ml of methanol and dried in vacuum, leaving 352 mg of 1-[2-(3,4-epoxycyclohexyl)ethyl]dimethylsiloxy-3,5,7,9,11,13,15-heptakis-20 (trimethylsiloxy)pentacyclo[9.5.1.1$^{3,9}$.1$^{5,15}$.1$^{7,13}$]octasiloxane as white solids. The yield was 95%. The results of identification by NMR, MALDI-TOFMS (matrix: cobalt) and GPC are shown below.

$^1$H-NMR (CDCl$_3$, 300 MHz): δ (ppm) 3.18-3.11 (2H, m), 2.22-1.94 (2H, m), 1.87-1.64 (1H, m), 1.55-0.82 (6H, m), 0.57-0.52 (2H, m), 0.15 (63H, s), 0.12 (6H, s+s)

$^{13}$C-NMR (CDCl$_3$, 75.6 MHz): δ (ppm) 53.2, 52.7, 52.0, 51.9, 35.4, 32.2, 31.5, 31.4, 29.8, 29.2, 26.6, 25.4, 24.0, 23.6, 14.6, 14.5, 1.3, 1.2, −0.5×3

$^{29}$Si-NMR (CDCl$_3$, 59.7 MHz): δ (ppm) 12.9, 12.5, −108.9, −109.0, −110.6

MALDI-TOFMS: m/z 1262.3 (M+Na$^+$)

GPC (based on polystyrene standard, RI detector):
$M_w$=1,208, $M_w/M_n$=1.005

Japanese Patent Application No. 2004-292386 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monofunctional monomer having a cage oligosiloxane structure, represented by the following general formula (1):

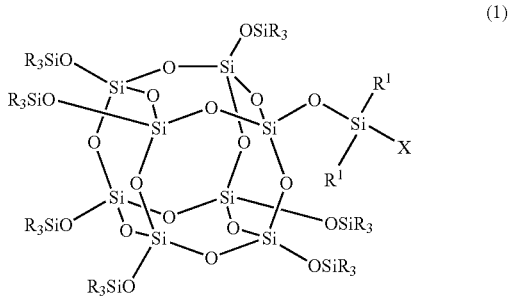

(1)

wherein X is a polymerizable group of 1 to 40 carbon atoms containing any one of a methacryloyl group, acryloyl group, epoxide or cyclic acid anhydride, R$^1$ is independently selected from the class consisting of saturated hydrocarbon groups of 1 to 20 carbon atoms, aromatic hydrocarbon groups of 6 to 20 carbon atoms, organoxy groups of 1 to 20 carbon atoms, and halogen atoms, the R groups bonded to a common silicon atom may be the same or different, wherein in formula (1), R is one selected from the group consisting of methyl, chloromethyl, ethyl, n-propyl, isopropyl, n-butyl, isobutyl, tert-butyl, pentyl, cyclopentyl, isopentyl, tert-pentyl, hexyl, cyclohexyl, 4-tert-butylcyclohexyl, 2-ethylhexyl, octyl, isooctyl, decyl, dodecyl, stearyl, hexadecyl, octadecyl, eicosyl, phenyl, 4-tert-butylphenyl, 3,5-di-tert-butylphenyl, 2-tolyl, 3-tolyl, 4-tolyl, 2,6-dimethylphenyl, 2,4-dimethylphenyl, 3,5-dimethylphenyl, 3,4-dimethylphenyl, 2,5-dimethylphenyl, naphthyl, biphenylyl, phenanthryl, anthracenyl, benzyl, 1-phenylethyl, 2-phenylethyl, and naphthylethyl.

2. A method for preparing a monofunctional monomer having a cage oligosiloxane structure, represented by the general formula (1) as set forth in claim 1, said method comprising reacting a cage oligosiloxane having a silanol site represented by the following general formula (2) with an organosilicon compound represented by the following general formula (3):

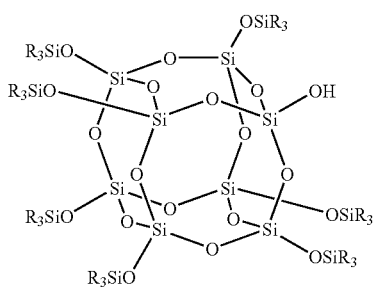
(2)

wherein R is one selected from the group consisting of methyl, chloromethyl, ethyl, n-propyl, isopropyl, n-butyl, isobutyl, tert-butyl, pentyl, cyclopentyl, isopentyl, tert-pentyl, hexyl, cyclohexyl, 4-tert-butylcyclohexyl, 2-ethylhexyl, octyl, isooctyl, decyl, dodecyl, stearyl, hexadecyl, octadecyl, eicosyl, phenyl, 4-tert-butylphenyl, 3,5-di-tert-butylphenyl, 2-tolyl, 3-tolyl, 4-tolyl, 2,6-dimethylphenyl, 2,4-dimethylphenyl, 3,5-dimethylphenyl, 3,4-dimethylphenyl, 2,5- dimethylphenyl, naphthyl, biphenylyl, phenanthryl, anthracenyl, benzyl, 1-phenylethyl, 2-phenylethyl, and naphthylethyl, the R groups bonded to a common silicon atom may be the same or different,

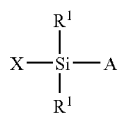
(3)

wherein X is a polymerizable group of 1 to 40 carbon atoms containing any one of a methacryloyl group, acryloyl group, epoxide or cyclic acid anhydride, A is an organoxy group of 1 to 20 carbon atoms or a halogen atom, and $R^1$ is independently selected from the class consisting of saturated hydrocarbon groups of 1 to 20 carbon atoms, aromatic hydrocarbon groups of 6 to 20 carbon atoms, organoxy groups of 1 to 20 carbon atoms, and halogen atoms.

3. A method for preparing a monofunctional monomer having a cage oligosiloxane structure, represented by the general formula (1) as set forth in claim 1, said method comprising reacting a cage oligosiloxane having a silanol site represented by the following general formula (2) with an organosilicon compound represented by the following general formula (4), and combining the reaction product with an unsaturated compound of up to 40 carbon atoms having at least one oxygen atom-containing polymerizable group represented by the following general formula (5) through hydrosilylation reaction:

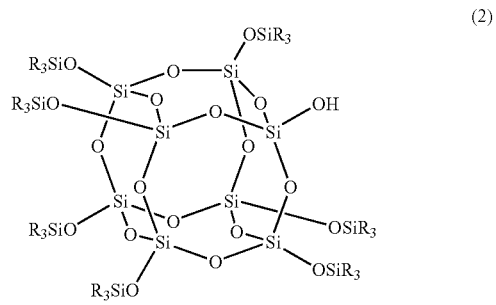
(2)

wherein R is one selected from the group consisting of methyl, chloromethyl, ethyl, n-propyl, isopropyl, n-butyl, isobutyl, tert-butyl, pentyl, cyclopentyl, isopentyl, tert-pentyl, hexyl, cyclohexyl, 4-tert-butylcyclohexyl, 2-ethylhexyl, octyl, isooctyl, decyl, dodecyl, stearyl, hexadecyl, octadecyl, eicosyl, phenyl, 4-tert-butylphenyl, 3,5-di-tert-butylphenyl, 2-tolyl, 3-tolyl, 4-tolyl, 2,6-dimethylphenyl, 2,4-dimethylphenyl, 3,5-dimeth_ylphenyl, 3 ,4-dimethylphen_yl, 2,5-dimethylphenyl, naphthyl, biphenylyl, phenanthryl, anthracenyl, benzyl, 1-phenylethyl, 2-phenylethyl, and naphthylethyl, the R groups bonded to a common silicon atom may be the same or different,

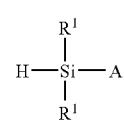
(4)

wherein A is an organoxy group of 1 to 20 carbon atoms or a halogen atom, and $R^1$ is independently selected from the class consisting of saturated hydrocarbon groups of 1 to 20 carbon atoms, aromatic hydrocarbon groups of 6 to 20 carbon atoms, organoxy groups of 1 to 20 carbon atoms, and halogen atoms,

(5)

wherein Z is a polymerizable monovalent organic group of 1 to 38 carbon atoms containing any one of a methacryloyl group, acryloyl group, epoxide or cyclic acid anhydride.

4. The monofunctional monomer of claim 1 wherein in formula (1), X is one selected from the group consisting of oxiranyl, 2,3-epoxypropyl, 3,4-epoxybutyl, 3,4-epoxycyclohexyl, 2,3-epoxycyclohexyl, glycidyloxypropyl, 3,4-epoxycyclohexylethyl, 3-ethyloxetan-3-ylmethyl, [3-(3-ethyloxetan-3-yl)methyloxy] propyl, acryloyloxypropyl, acryloyloxymethyl, methacryloyloxypropyl, methacryloyloxymethyl, acryloylaminomethyl, acryloylaminopropyl, methacryloylaminomethyl, methacryloylaminopryl, acryloylthiopropyl, methacryloylthiopropyl, tetrahydrofuran-2, 5-dion-3-ylpropyl and 1,3-dihydroisobenzofuran-1,3-dion-5-yl.

5. The method of claim 2 wherein in formula (1), X is one selected from the group consisting of oxiranyl, 2,3-epoxypropyl, 3,4-epoxybutyl, 3,4epoxycyclohexyl, 2,3- epoxycyclohexyl, glycidyloxypropyl, 3,4-epoxycyclohexylethyl, 3-ethyloxetan-3-ylmethyl, [3-(3-ethyloxetan-3-yl)methyloxy] propyl, acryloyloxypropyl, acryloyloxymethyl, methacryloyloxypropyl, methacryloyloxymethyl, acryloylaminomethyl, acryloylaminopropyl, methacryloylaminomethyl, methacryloylaminopryl, acryloylthiopropyl, methacryloylthiopropyl, tetrahydrofuran-2,5-dion-3-ylpropyl and 1,3-dihydroisobenzofuran-1,3-dion-5-yl.

6. The method of claim 3 wherein in formula (5), Z is one selected from the group consisting of oxiranyl, 2,3-epoxypropyl, 3,4-epoxybutyl, 3,4epoxycyclohexyl, 2,3- epoxycyclohexyl, glycidyloxypropyl, 3,4-epoxycyclohexylethyl, 3-ethyloxetan-3-ylmethyl, [3-(3-ethyloxetan-3-yl)methyloxy] propyl, acryloyloxypropyl, acryloyloxymethyl, methacryloyloxypropyl, methacryloyloxymethyl, acryloylaminomethyl, acryloylaminopropyl, methacryloylaminomethyl, methacryloylaminopryl, acryloylthiopropyl, methacryloylthiopropyl, tetrahydrofuran-2,5-dion-3-ylpropyl and 1,3-dihydroisobenzofuran-1,3-dion-5-yl.

7. The monofunctional monomer having a cage oligosiloxane structure, as set forth in claim 1, wherein $R^1$ is at least one of the group consisting of methyl, ethyl, n-propyl, isopropyl, n-butyl, isobutyl, tert-butyl, pentyl, cyclopentyl, isopentyl, tert-pentyl, hexyl, cyclohexyl, 2-ethylhexyl, octyl, isooctyl, decyl, dodecyl, stearyl, phenyl, 4-tert-butylphenyl, 2-tolyl, 3-tolyl, 4-tolyl, 2,6-dimethylphenyl, 2,4-dimethylphenyl, 3,5-dimethylphenyl, 3,4-dimethylphenyl, 2,5-dimethylphenyl, naphthyl, biphenylyl, benzyl, 1-phenylethyl, 2-phenylethyl naphthylethyl, methoxy, ethoxy, n-propoxy, isopropoxy, n-butoxy, isobutoxy, tert-butoxy, pentyloxy, cyclopentyloxy, isopentyloxy, tert-pentyloxy, hexyloxy, cyclohexyloxy, 2-ethylhexyloxy, octyloxy, isooctyloxy, decyloxy, dodecyloxy, stearyloxy, phenoxy, 4-tert-butylphenoxy, 2-tolyloxy, 3-tolyloxy, 4-tolyloxy, 2,6-dimethylphenoxy, 2,4-dimethylphenoxy, 3,5-dimethylphenoxy, 3,4-dimethylphenoxy, 2,5-dimethylphenoxy, naphthyloxy, biphenylyloxy, benzyloxy, phenylethyloxy, fluoro, chloro, bromo and iodo.

\* \* \* \* \*